United States Patent
Yoda et al.

(10) Patent No.: US 9,116,225 B2
(45) Date of Patent: Aug. 25, 2015

(54) MEASURING APPARATUS

(75) Inventors: Haruo Yoda, Nishitama-gun (JP); Katsuya Oikawa, Tokyo (JP); Kenichi Nagae, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 866 days.

(21) Appl. No.: 13/266,981

(22) PCT Filed: Apr. 28, 2010

(86) PCT No.: PCT/JP2010/057916
§ 371 (c)(1),
(2), (4) Date: Oct. 28, 2011

(87) PCT Pub. No.: WO2010/137451
PCT Pub. Date: Dec. 2, 2010

(65) Prior Publication Data
US 2012/0044785 A1 Feb. 23, 2012

(30) Foreign Application Priority Data

May 25, 2009 (JP) ................................. 2009-124888

(51) Int. Cl.
*G01S 7/52* (2006.01)
*G01S 15/00* (2006.01)
(Continued)

(52) U.S. Cl.
CPC ......... *G01S 7/52046* (2013.01); *G01S 7/52085* (2013.01); *G01S 15/8909* (2013.01);
(Continued)

(58) Field of Classification Search
CPC ............ G01S 7/52046; G01S 7/52085; G01S 15/8909; G01S 15/8934; G01S 15/8945; G01S 15/8997; G01S 15/8915; G10K 11/346; G10K 11/352; A61B 5/483
USPC .............................. 367/11, 105; 600/447, 459
See application file for complete search history.

(56) References Cited

U.S. PATENT DOCUMENTS 4,324,142 A * 4/1982 Auphan et al. .................. 73/626
4,542,746 A 9/1985 Takamizawa
(Continued)

FOREIGN PATENT DOCUMENTS

CN 1785124 6/2006
EP 0 087 318 A2 8/1983
(Continued)

OTHER PUBLICATIONS

Office Action issued Mar. 12, 2013 in counterpart Chinese Patent Application No. 201080022646.X, with translation.
(Continued)

*Primary Examiner* — Luke Ratcliffe
*Assistant Examiner* — Hovhannes Baghdasaryan
(74) *Attorney, Agent, or Firm* — Fitzpatrick, Cella, Harper & Scinto (57) ABSTRACT

Provided is a measuring apparatus, including: a moving mechanism for moving a probe in an elevation direction; a first delay and sum circuit for performing delay and sum of reception signals at individual positions along the elevation direction to output a first add signal; a signal extraction circuit for letting an output of the first delay and sum circuit to pass through delay circuits to output in parallel first add signals obtained at different positions; a second delay and sum circuit for performing delay and sum of the first add signals output from the signal extraction circuit to output a second add signal; and an image processing circuit for generating image data by using the second add signal. Accordingly, image resolution in the elevation direction may be improved with a simple structure without deteriorating an image obtaining speed in the measuring apparatus for obtaining an ultrasonic image.

9 Claims, 9 Drawing Sheets

(51) Int. Cl.
*G01S 15/89* (2006.01)
*G10K 11/34* (2006.01)
*G10K 11/35* (2006.01)
*A61B 8/08* (2006.01)

(52) U.S. Cl.
CPC ......... *G01S15/8915* (2013.01); *G01S 15/8934* (2013.01); *G01S 15/8945* (2013.01); *G01S 15/8997* (2013.01); *G10K 11/346* (2013.01); *G10K 11/352* (2013.01); *A61B 8/483* (2013.01); *G01S 15/8993* (2013.01)

(56) References Cited

U.S. PATENT DOCUMENTS

| | | | |
|---|---|---|---|
| 5,186,175 A | 2/1993 | Hirama et al. | 600/447 |
| 6,258,030 B1 | 7/2001 | Hirama | 600/443 |
| 8,298,144 B2 | 10/2012 | Burcher | |
| 2005/0187471 A1* | 8/2005 | Kanayama et al. | 600/437 |
| 2006/0184019 A1 | 8/2006 | Ito et al. | 600/437 |
| 2008/0306371 A1 | 12/2008 | Fukutani et al. | 600/407 |
| 2009/0005685 A1 | 1/2009 | Nagae et al. | 600/459 |
| 2009/0043209 A1* | 2/2009 | Hirama | 600/459 |
| 2009/0118614 A1 | 5/2009 | Sendai | 600/437 |
| 2009/0177088 A1 | 7/2009 | Hasegawa et al. | 600/445 |
| 2009/0187099 A1 | 7/2009 | Burcher | |
| 2009/0275837 A1 | 11/2009 | Shiina et al. | 600/459 |
| 2009/0299185 A1 | 12/2009 | Oikawa et al. | 600/447 |
| 2011/0083511 A1 | 4/2011 | Taki et al. | 73/602 |
| 2011/0128816 A1 | 6/2011 | Baba et al. | 367/11 |
| 2011/0208035 A1 | 8/2011 | Baba et al. | 600/407 |
| 2011/0208057 A1 | 8/2011 | Oikawa | 600/443 |
| 2011/0307181 A1 | 12/2011 | Nagae | 702/19 |

FOREIGN PATENT DOCUMENTS

| | | |
|---|---|---|
| JP | 05-146444 | 6/1993 |
| JP | 05-344975 | 12/1993 |
| JP | H06-125895 A | 5/1994 |
| JP | H07-236642 A | 9/1995 |
| JP | 2006-102494 | 5/2006 |
| JP | 2008-161283 | 7/2008 |
| WO | 2007/148239 A2 | 12/2007 |
| WO | WO 2008/026332 | 3/2008 |

OTHER PUBLICATIONS

L. Song et al., "Fast 3-D Dark-Field Reflection-Mode Photoacoustic Microscopy in vivo with a 30-MHz Ultrasound Linear Array", *Journal of Biomedical Optics*, vol. 13, No. 5, Sep./Oct. 2008, pp. 054028-1 through 054208-5.

A. Aguirre et al., "Feasibility Study of Three-Dimensional Co-Registered Ultrasound and Photoacoustic Imaging for Cancer Detection and Visualization", *Proc. of SPIE* vol. 6856, 2008, pp. 68562A-1-68562A-10.

Japanese Office Action issued in counterpart application No. 2013-214784 dated Jul. 1, 2014, along with its English-language translation—6 pages.

European Communication issued in corresponding application No. 10722791.0 dated Feb. 23, 2015 (7 pages).

* cited by examiner

MEASURING APPARATUS

TECHNICAL FIELD

The present invention relates to a measuring apparatus which obtains information inside an object using an acoustic wave, and more particularly, to a measuring apparatus having a probe that is mechanically scanned.

BACKGROUND ART

Conventionally, as an effective image diagnosis apparatus for early detection of breast cancer, there is known an x-ray mammography apparatus. Further, in recent years, there is developed a photoacoustic imaging method in which a pulse laser beam is irradiated onto a living body instead of an X-ray, so as to image a three-dimensional structure inside the living body based on a photoacoustic wave induced by thermal expansion of an optical absorber inside the living body. This apparatus has received attention as a new mammography apparatus that may easily diagnose a potential tumor such as an abnormal growth of new blood vessels.

Such a mammography apparatus has a feature that an abnormal region which is difficult to detect by other apparatus may be detected as a clear image. However, for precise diagnosis of an early cancer, it is usually necessary to use both a mammography image and an ultrasonic echo image in combination. In view of this, for example, Japanese Patent Application Laid-Open No. 2006-102494 and Japanese Patent Application Laid-Open No. 2008-161283 disclose examples of an x-ray mammography apparatus incorporating an ultrasonic diagnosis apparatus. In these apparatuses, a breast as an object is fixed to a compression plate, and a mammography sensor and an ultrasonic probe are moved mechanically for scanning along the compression plate so that a mammography image and a three-dimensional ultrasonic echo image of the entire breast may be obtained simultaneously.

In obtaining three-dimensional echo image data of a wide area with mechanically scanning the ultrasonic probe, it is most advantageous in speed and cost to move a one-dimensionally arranged probe in a direction perpendicular to the arrangement direction of elements or in a direction crossing the same (hereinafter, referred to as elevation direction) continuously while obtaining the echo image data. Using the one-dimensionally arranged probe, it is possible to reconstruct a cross-sectional slice image by electronic scanning in the arrangement direction and in an ultrasonic beam emitting direction. Therefore, there may be obtained three-dimensional image data of the entire mechanical scan area by stacking the cross-sectional slice images generated at individual positions in the elevation direction.

However, this method has a problem that image resolution in the elevation direction significantly reduces as compared with image resolution in a slice plane. A first reason is that if the mechanical scan speed by the probe is decreased so as to reduce a pitch of obtaining the cross-sectional slice images, it may increase a physical load to the human object. Therefore, it is necessary to lower the pixel density in the elevation direction to some extent. In addition, a second reason is that effective angular aperture of the one-dimensionally arranged probe in the elevation direction is smaller than that in the arrangement direction, so that a reconstruction resolution in the elevation direction is deteriorated. If a two-dimensionally arranged probe is used, this problem may be alleviated to some extent. However, the number of transmission and reception elements increases, which leads to another problem that a necessary electric circuit scale increases, making it difficult to achieve the practical use of the apparatus in terms of cost.

DISCLOSURE OF THE INVENTION

An object of the present invention is to improve image resolution in the elevation direction with a simple structure without deteriorating a speed of obtaining image data in a measuring apparatus for obtaining image data while moving a probe in the elevation direction continuously.

A measuring apparatus according to the present invention includes: a probe having a plurality of elements for converting an acoustic wave into an electric signal, the plurality of elements being arranged in at least first direction (arrangement direction of the elements); a moving mechanism for moving the probe in a second direction (elevation direction) crossing the first direction along a subject surface; a first delay and sum circuit for performing delay and sum of the electric signals obtained by the plurality of elements at individual positions along the second direction, so as to output a first add signal; a signal extraction circuit for letting an output of the first delay and sum circuit to pass through at least one delay circuit, so as to output in parallel a plurality of first add signals obtained at different positions; a second delay and sum circuit for performing delay and sum of the plurality of first add signals output from the signal extraction circuit, so as to output a second add signal; and an image processing circuit for generating image data inside a subject by using the second add signal.

According to the present invention, image resolution in the elevation direction may be improved with a simple structure without deteriorating a speed of obtaining image data in the measuring apparatus for obtaining image data while moving the probe in the elevation direction continuously.

Further features of the present invention will become apparent from the following description of exemplary embodiments with reference to the attached drawings.

BEST MODE FOR CARRYING OUT THE INVENTION

A measuring apparatus according to the present invention is an apparatus for obtaining information inside an object by using an acoustic wave (typically an ultrasonic wave), which is used as a medical ultrasonic diagnosis apparatus and the like, for example. The measuring apparatus of the present invention has a basic structure including a probe in which a plurality of elements for converting an acoustic wave into an electric signal are arranged, and a moving mechanism for moving the probe (for mechanical scan) along a surface of the object in an elevation direction. Note that the probe may be either a one-dimensionally arranged probe having a plurality of elements arranged in one-dimensional manner or a two-dimensionally arranged probe having a plurality of elements arranged in two-dimensional manner (in a matrix). However, for downsizing and cost reduction of the apparatus, it is preferable to use the one-dimensionally arranged probe. Usually, the elevation direction (second direction) is set so as to cross (perpendicular to or substantially perpendicular to) the arrangement direction of elements (first direction).

In order to improve image resolution in the elevation direction, it is necessary to perform two-dimensional delay and sum by using input signals of successive cross-sectional slice planes. The two-dimensional delay and sum includes delay and sum in the arrangement direction of probe elements (first direction) and delay and sum in the elevation direction (second direction). However, the one-dimensionally arranged probe moves continuously so that individual slice planes have different transmission and reception timings of the acoustic wave. Therefore, it is necessary to regard the delay and sum in the arrangement direction as normal delay and sum and the delay and sum in the elevation direction as delay and sum based on the synthetic aperture method. Note that the delay and sum refers to a process of adjusting phases of a plurality of signals according to a propagation distance of the acoustic wave between a target point (focal point) and a reception point, and then summing (combining) the plurality of signals so as to obtain the signal indicating information of the target point.

The present invention realizes the two-dimensional delay and sum by additionally including a relatively small circuit. According to the present invention, first, the one-dimensionally arranged probe is mechanically moved continuously along a surface of the object while the first delay and sum circuit repeats the one-dimensional delay and sum of the reception signal in the arrangement direction, so that the delay and sum is performed for each cross-sectional slice plane. The cross-sectional slice plane is a plane which is parallel to the arrangement direction of elements and crosses (is perpendicular to) the elevation direction. Thus, at individual positions along the elevation direction, delay and sum signals (first add signals) of a plurality of cross-sectional slice planes are calculated and delivered periodically. Then, the delay and sum signals delivered from the first delay and sum circuit are led to pass through one or more delay circuits so that the delay and sum signals at the corresponding positions of a plurality of successive cross-sectional slice planes are extracted in parallel. A delay time of the delay circuit may be set to a time corresponding to a scanning period for one slice plane. If two or more delay circuits are combined, the delay circuits are cascaded so that an output of a first delay circuit is supplied to an input of a second delay circuit. A plurality of delay and sum signals that are extracted in the manner as described above are delayed and summed in the elevation direction by the second delay and sum circuit, to thereby obtain a second add signal. The image processing circuit uses the second add signal so as to generate the image data.

Note that an apparatus which moves the one-dimensional probe mechanically for scanning so as to generate three-dimensional image data is disclosed in Japanese Patent Application Laid-Open No. H05-344975, which has an apparatus structure in which the whole reception data is temporarily recorded in the waveform memory, and later the delay and sum process is performed based on the synthetic aperture method. However, this apparatus structure has a problem that a large-capacity waveform memory is necessary and it is difficult to perform a real-time process of the image reconstruction.

Japanese Patent Application Laid-Open No. H05-146444 discloses a method of performing the two-dimensional delay and sum by cascade coupling of one-dimensional delay and sum. A purpose of this known example is to reduce a circuit scale of the delay and sum circuit for performing parallel delay and sum of output signals from the transmission and reception elements arranged in a matrix in the two-dimensionally arranged probe. For this purpose, first, the transmission and reception elements are driven by one column at a time for performing delay and sum, and a result thereof is stored in the memory. Then, the memory is read out so as to perform delay and sum in the row direction. However, this known example does not refer at all to a concept for obtaining three-dimensional image data of a large area by moving a probe mechanically. In addition, this apparatus structure also requires a relatively large capacity memory for storing data of individual columns and causes the problem that the real-time process of the image reconstruction is difficult.

The measuring apparatus of the present invention includes (1) a circuit for performing delay and sum of the reception signal, (2) a circuit for extracting delay and sum signals of a plurality of cross-sectional slice planes at the corresponding positions in parallel by using the delay circuit, and (3) a circuit for performing delay and sum of the plurality of delay and sum signal extracted in the elevation direction. With this structure, image resolution in the elevation direction may be improved with a relatively small circuit, without impairing real-time property.

Note that the first delay and sum according to the present invention is a process for calculating the delay and sum signals in the individual cross-sectional slice planes. Therefore, if a two-dimensionally arranged probe having elements arranged in a two-dimensional manner is used, the first delay and sum circuit may be structured so as to calculate the delay and sum signals in one or more cross-sectional slice planes by the two-dimensional delay and sum. Alternatively, the two-dimensionally arranged probe may be used as a one-dimensionally arranged probe by driving only one column of elements in the two-dimensionally arranged probe so as to obtain one-dimensional reception signal.

Further, the present invention may be similarly applied, not only to a reflected wave generated by reflection of the transmission ultrasonic wave, but also to a photoacoustic wave induced inside the object by a pulse-like electromagnetic wave radiated from a pulse laser. In this case, first, an electromagnetic wave source and a probe are moved continuously as one unit, so that the acoustic wave induced by the electromagnetic wave is received by the probe. In this manner, the three-dimensional photoacoustic image data may be generated by the same process as the case of the ultrasonic wave. In other words, the "acoustic wave" in the present invention is a concept which includes not only the reflected wave of the ultrasonic wave transmitted to the object (echo ultrasonic wave) but also the photoacoustic wave generated by expansion of an optical absorber inside the living body caused by the pulse light irradiated onto the object.

According to the structure of the present invention described above, the three-dimensional ultrasonic wave image data of a wide area may be obtained by moving the probe for mechanical scanning. Further, with the addition of only a small and inexpensive circuit constituted of one or more delay circuits, image resolution in the elevation direction may be improved without impairing real-time property of the delay and sum process and the image reconstruction process. Therefore, with a relatively inexpensive apparatus using mechanical scan of the one-dimensionally arranged probe, there may be realized a measuring apparatus capable of obtaining high resolution and uniform three-dimensional ultrasonic wave image data at high speed. Further, the apparatus adopts the method of moving the small probe continuously, which makes it easy to use the apparatus together with a mammography apparatus which moves a sensor at a constant speed.

EXAMPLE 1

(Transmission of Ultrasonic Wave)

Figure 1:
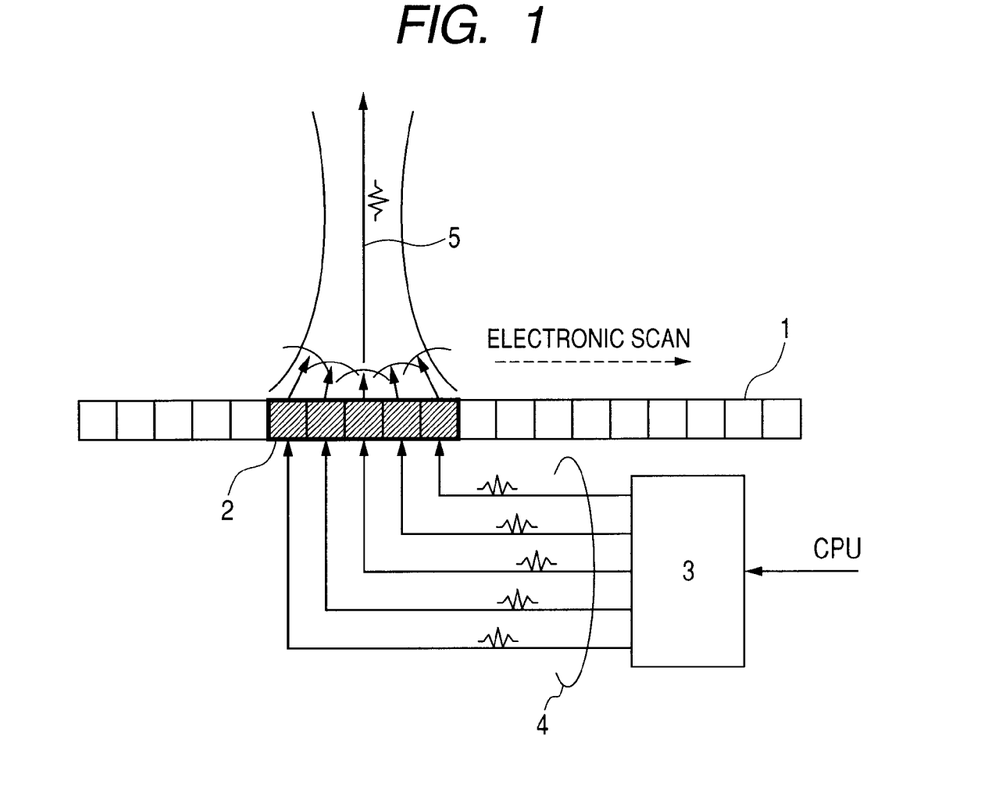
FIG. 1 is a diagram illustrating a structure of a transmission process of a measuring apparatus according to Example 1.
Figure 2:
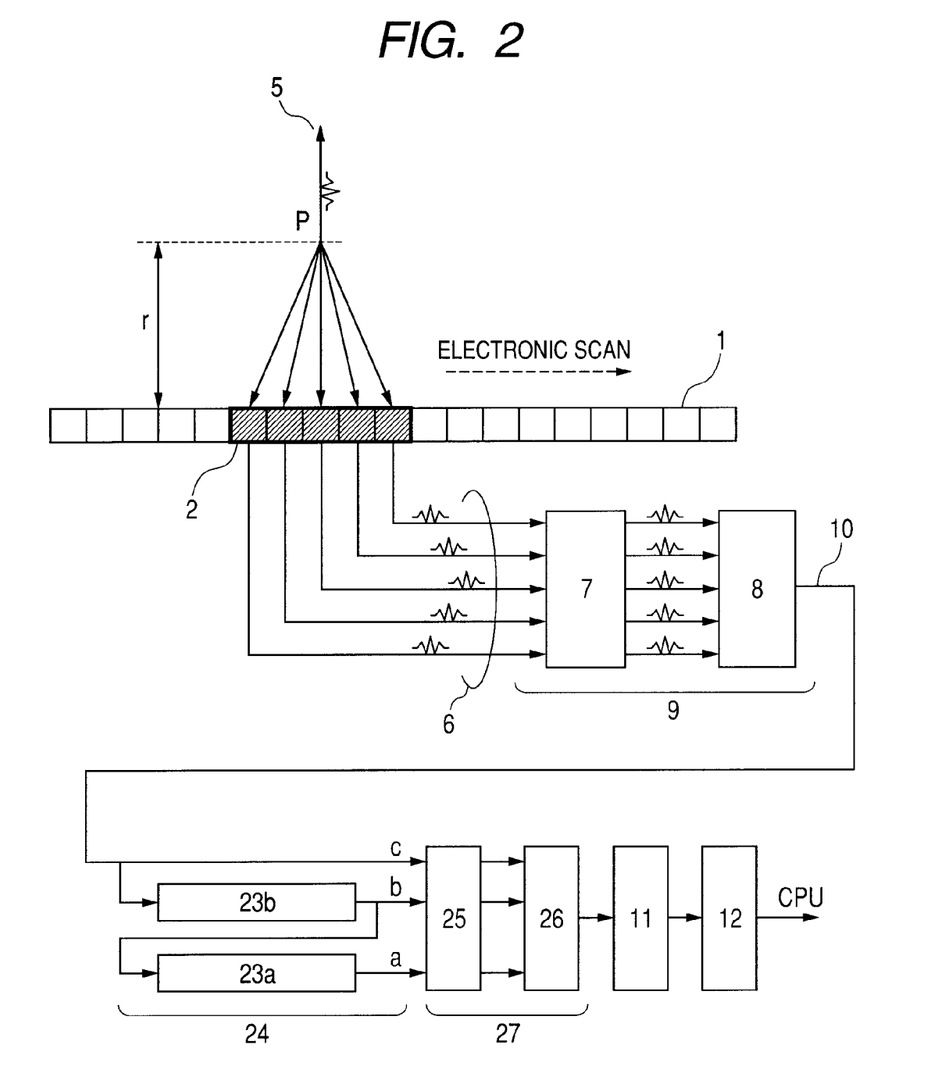
FIG. 2 is a diagram illustrating a structure of a reception process of the measuring apparatus according to Example 1.

With reference to FIGS. 1 and 2, Example 1 of the present invention is described. FIG. 1 is a diagram illustrating a principle of a linear scanning method of transmitting an ultrasonic beam 5 using a one-dimensionally arranged probe 1 (hereinafter, simply referred to as "probe"). The ultrasonic wave beam may also be emitted from one transmission and reception element of the probe 1. However, usually, as illustrated in FIG. 1, a plurality of transmission and reception elements are driven (hereinafter, a group of elements to be driven is referred to as "transmission and reception element group 2"), so as to emit a high intensity and high directivity ultrasonic beam 5. In this case, a transmission control circuit 3 applies a pulse-like drive signal 4 to individual transmission and reception elements of the transmission and reception element group 2 at individual timings, so that each transmission and reception element is applied with the drive signal 4 a little earlier with increasing distance outward from the transmission center position. As a result, ultrasonic waves emitted from the individual transmission and reception elements propagate in a direction converging toward the center part as illustrated in FIG. 1, so that a high intensity transmission beam 5 is formed as a whole so as to emit from the center part of the transmission and reception element group 2.

Immediately after emitting the pulse-like ultrasonic wave, the transmission and reception element group 2 switches from the transmission operation to the reception operation, so as to receive the ultrasonic echo (reflected wave) that is reflected inside the object as described later. After finishing the reception, an adjacent transmission and reception element group is selected by a switch circuit (not shown), which performs the same transmission and reception operation as a new transmission and reception element group 2. In this way, the transmission and reception element group 2 is moved sequentially from the left end to the right end of the probe 1 while the transmission and reception operation is repeated. Thus, the transmission beam 5 may perform sequential electronic scan of the inside of the cross-sectional slice plane perpendicular to the surface of the probe.

(Reception of Ultrasonic Wave)

FIG. 2 is a diagram illustrating a structure relating to a reception process performed by the measuring apparatus according to Example 1. The measuring apparatus includes a first delay and sum circuit 9, a signal extraction circuit 24, a second delay and sum circuit 27, a detection circuit 11, an image memory 12, and a CPU. The first delay and sum circuit 9 includes a delay adjustment circuit 7 and an add circuit 8. The signal extraction circuit 24 includes delay circuits 23a and 23b. The second delay and sum circuit includes a delay adjustment circuit 25 and an add circuit 26.

First, with reference to FIG. 2, an operation of the measuring apparatus for receiving the reflected wave is described. It is supposed that the transmission beam 5 is reflected at a point P at a position of a distance r and is received by the transmission and reception element group 2. Then, the reception signals 6 output from the individual transmission and reception elements are shifted in time according to a propagation distance of the reflected wave. In other words, each element of the transmission and reception element group 2 outputs the reception signal 6 of the reflected wave reflected from the point P with more delay as being apart outward from the center position of the transmission and reception element group 2. Therefore, with reference to the signal output from the transmission and reception element at the center position of the transmission and reception element group 2, delay times of the reception signals 6 output from the individual transmission and reception elements are adjusted by the delay adjustment circuit 7, so that reflection signal components from the point P included in the reception signals of the individual transmission and reception elements are added by the add circuit 8. Thus, a high intensity signal with a focal point of the point P may be obtained. The reception element receives ultrasonic echoes (reflected waves) superimposed from various directions, but a sum of the signals of the ultrasonic echoes from other points does not become a large signal component because they have nonuniform phases of the reception waves.

Figure 3:
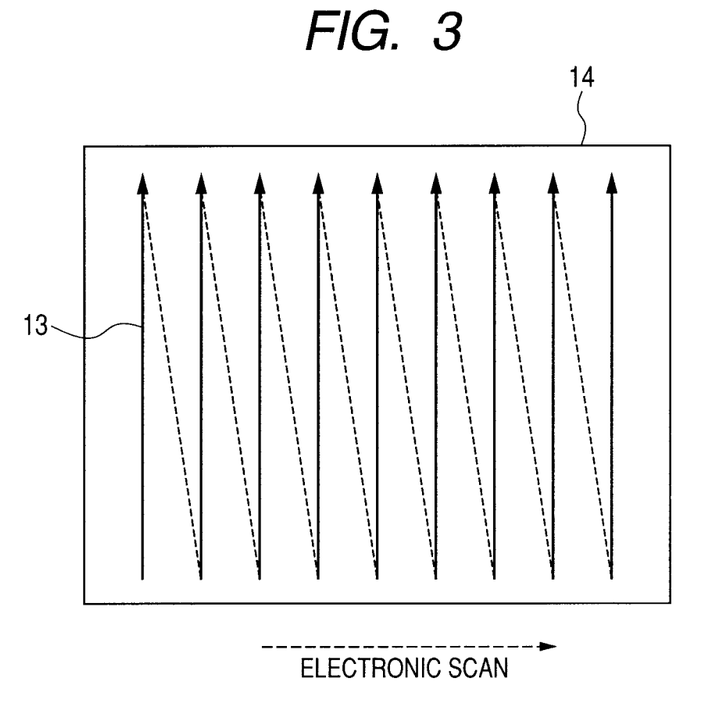
FIG. 3 is a diagram illustrating a signal in a cross-sectional slice plane obtained by electronic scan.

A time t at which the reflected wave from the point P of the distance r is received at the center position of the transmission and reception element group 2 may be expressed as $t=2r/c$, where c denotes known sound velocity. Therefore, the distance r to the corresponding reflection position may be calculated based on the time t, and the signal delay time of each element may be calculated based on the calculated r. If the adjustment of delay times is performed appropriately by the delay adjustment circuit 7 according to the corresponding distance r in real time together with the reception time t, high intensity one-dimensional reflection signal waveform may be formed with adjusted focus at every points. As a result, a reflection signal waveform of the one-dimensional area along the transmission beam path, that is, an ultrasonic echo signal 10 may be formed. Therefore, if the transmission and reception of the ultrasonic beam is repeated by the above-mentioned electronic scanning method, a one-dimensional echo signal 13 of a raster scanning format is output as illustrated in FIG. 3, so that the ultrasonic echo signal of a cross-sectional slice plane 14 may be obtained.

The output echo signal is a signal having a frequency component of a transmission wave. Therefore, the echo signal is converted into envelope intensity by the detection circuit 11 and is temporarily stored in the image memory 12. Then, the CPU reads contents of the image memory 12 so that the ultrasonic echo image of the cross-sectional slice is displayed on an image display device (not shown). In other words, in this example, the detection circuit 11, the image memory 12, and the CPU constitute the image processing circuit.

Note that, when adding the input signals, the add circuit 8 may also weight each input signal according to a position where the signal is obtained. The weighted adding process is called an apodizing process. The apodizing process has an effect of controlling a reception aperture and reducing influence of interference waves on the periphery. The weight may be fixed or variable according to reception time, depending on the purpose.

(Mechanical Scan)

Figure 4A:
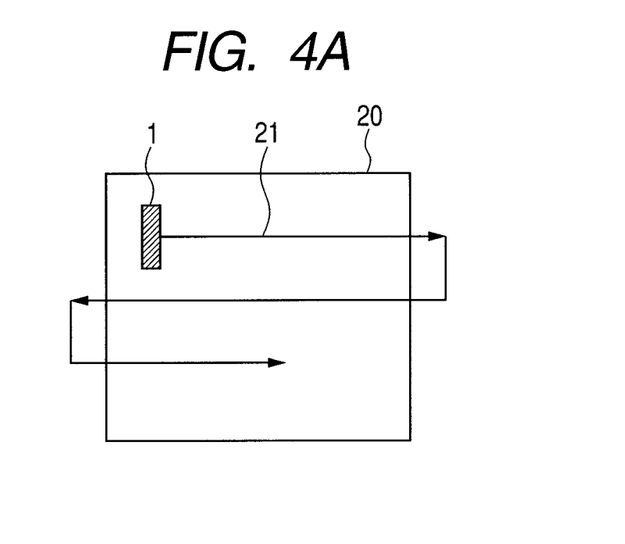
FIGS. 4A and 4B are diagrams each illustrating a mechanical scan path and a signal obtained by the mechanical scan, respectively.

FIG. 4A is a diagram illustrating an operation of moving the probe 1 along a route 21 in the elevation direction mechanically so as to obtain three-dimensional echo image data of a wide inspection area 20. Note that a known mechanism may be used as a moving mechanism of the probe 1, so illustration and detailed description thereof are omitted. The probe 1 is moved as illustrated in FIG. 4A at a constant speed, so that the cross-sectional slice image is obtained repeatedly at individual positions on the route 21. Then, the obtained cross-sectional slice images are closely arranged, so that the three-dimensional echo image of the entire inspection area may be obtained.

Figure 4B:
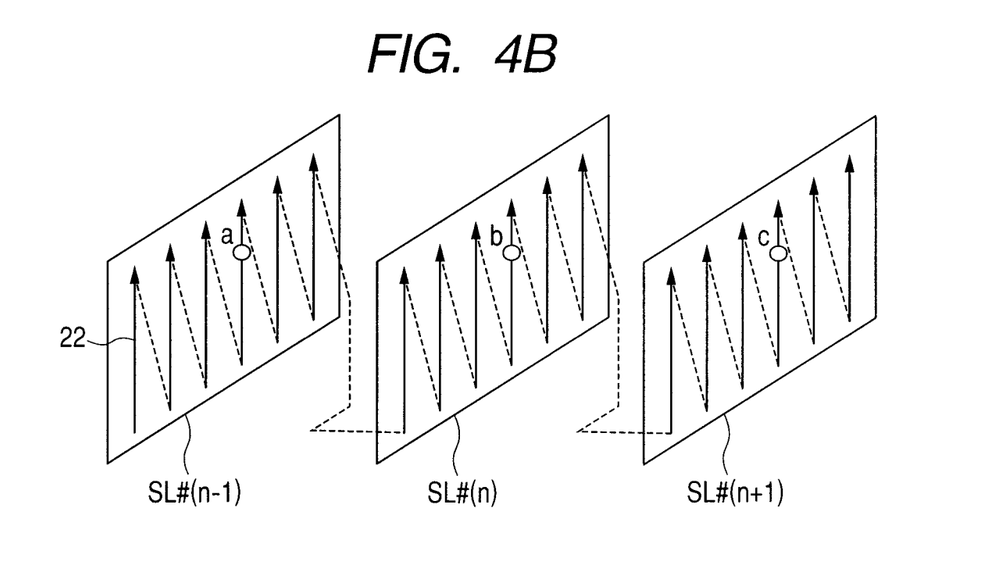

FIG. 4B illustrates scanning order of the output ultrasonic echo signal 22 when the cross-sectional slice planes are output in the order of . . . , SL#(n−1), SL#(n), SL#(n+1), . . . , while the probe 1 is moving continuously in the elevation direction. As illustrated in FIG. 4B, the echo signal 22 illustrated by the solid line of each ultrasonic wave transmission is calculated and output in the raster scanning order by the electronic scan inside each of the cross-sectional slice planes, and the cross-sectional slice planes are calculated and output at a constant period in the elevation direction. As a result, the echo signals at specific positions a, b and c in the cross-sectional slice planes are output at the constant period. In this case, the probe may move intermittently by a step and repeat method or may move continuously. If it moves continuously, the cross-sectional slice plane is not exactly perpendicular to the moving direction. However, for easy understanding, the cross-sectional slice plane is assumed herein to be perpendicular thereto.

(Two-Dimensional Delay and Sum)

With reference to FIG. 2 again, the two-dimensional delay and sum is described. In Example 1, the signal extraction circuit 24 including the delay circuits 23a and 23b, and the second delay and sum circuit 27 are added in the subsequent stage of the first delay and sum circuit 9, so that the two-dimensional delay and sum may be realized. The delay circuits 23a and 23b are cascaded, so that an output of the first delay and sum circuit 9 (the first add signal) is supplied to the delay circuit 23b, and an output of the delay circuit 23b is supplied to the delay circuit 23a. The delay times of the delay circuits 23a and 23b are each set to a value corresponding to a scanning period for one slice plane. The first delay and sum circuit 9 outputs an ultrasonic echo signal in the order illustrated in FIG. 4B. Accordingly, the signal extraction circuit 24 outputs in parallel the echo signals of the successive slice planes at the same position as illustrated by a, b and c of FIG. 4B. Therefore, if the delay adjustment circuit 25 and the add circuit 26 are set in the subsequent stage of the signal extraction circuit 24, the delay and sum in the elevation direction may be performed.

In Example 1, the delay time of the delay circuits 23a and 23b is set to a constant value supposing that a scanning period for the slice plane (scan repeating pitch) is constant. However, if the repeating pitch is disturbed or if the time is wasted for a certain reason, there may be added a unit for controlling start and stop of the delay circuits 23a and 23b appropriately, so that echo signals at the same position of the successive cross-sectional slice planes may always be output in parallel. In addition, both the delay circuits 23a and 23b, and the delay adjustment circuit 25 are circuits for adjusting delay times. Therefore, the circuits may be integrated into one delay adjustment circuit, or a method of dividing the delay time may be changed variously. Such a modification does not change the spirit of the present invention.

Figure 5A:
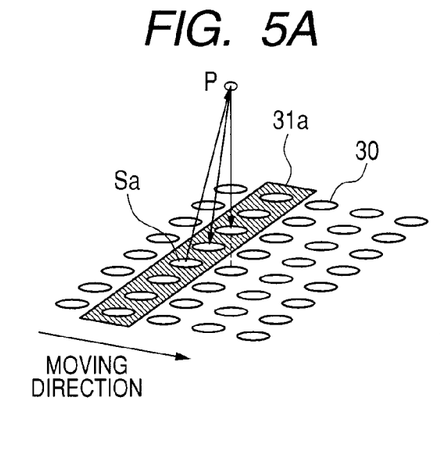
FIGS. 5A, 5B, 5C, and 5D are explanatory diagrams of a synthetic aperture method.
Figure 5B:
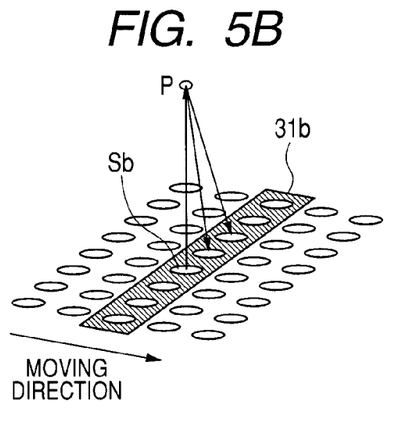
Figure 5C:
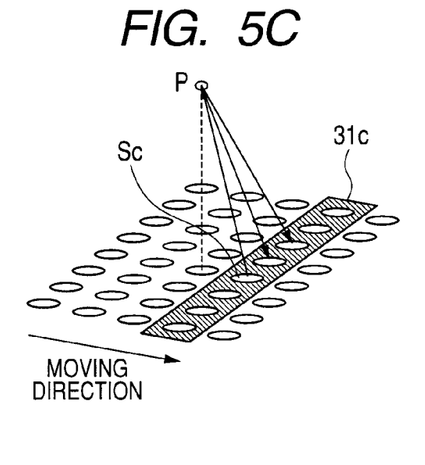

FIGS. 5A, 5B, 5C, and 5D are diagrams illustrating a principle of the synthetic aperture method. Small oval FIGS. 30 arranged in the diagrams indicate positions of the transmission and reception elements when the individual cross-sectional slice planes are scanned, and the point P indicates an arbitrary target point in the three-dimensional space. FIG. 5A illustrates a time point when the transmission and reception element group indicated by a rectangular FIG. 31a scans (n−1)th cross-sectional slice plane. A part of the ultrasonic wave beam emitted from the center part Sa propagates in the direction toward the point P, and a reflected wave thereof is received by the transmission and reception elements at the positions falling within the rectangular FIG. 31a. FIG. 5B illustrates a state in which the probe has moved to the n-th cross-sectional slice position. The transmission and reception element group falling within the rectangular FIG. 31b emits the ultrasonic wave beam from the center part Sb so that a part thereof also propagates in the direction toward the point P, and a reflected wave thereof is received by the transmission and reception element group in the position of the rectangular FIG. 31b. FIG. 5C illustrates a state in which the transmission and reception element group in the position of the rectangular FIG. 31c transmits and receives the ultrasonic wave with respect to the point P.

Figure 5D:
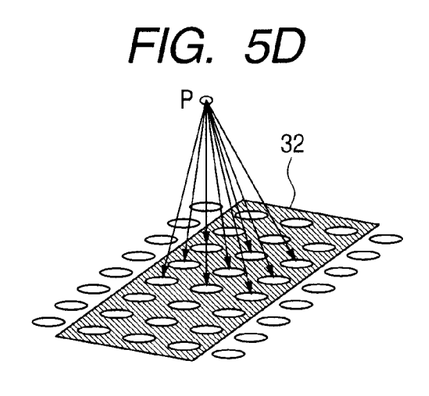

The transmission and reception time point is different among the cross-sectional slice planes. Here, the time period from the transmission to the reception is calculated based on the propagation distance and the sound velocity so as to adjust a signal reception time to be added to each reception element, to thereby add the signals from the same point P. As a result, as illustrated in FIG. 5D, there may be obtained a result equivalent to the case where signals received by a virtual two-dimensional probe constituted of a transmission and reception element group falling within a rectangular FIG. 32 are calculated by the two-dimensional delay and sum. In this manner, despite the use of the one-dimensional probe, there may be obtained echo image data having a resolution close to that in the case where a two-dimensional probe is used, which makes it possible, in particular, to improve a resolution in the elevation direction. This method of obtaining the performance equivalent to that in the case where reception signals of different ultrasonic wave transmission times are combined so as to increase the reception aperture substantially is a known technique as a synthetic aperture method.

Therefore, if all the reception signals of the transmission and reception elements in the past scanning are stored in the memory device, and if the reception signals two-dimensionally arranged are read out from the memory device simultaneously so as to perform the two-dimensional delay and sum, the resolution in the elevation direction may be improved. However, this method has a problem of apparatus cost because a large-capacity memory device and a circuit for performing delay and sum of many reception signals in real time are necessary.

Figure 6:
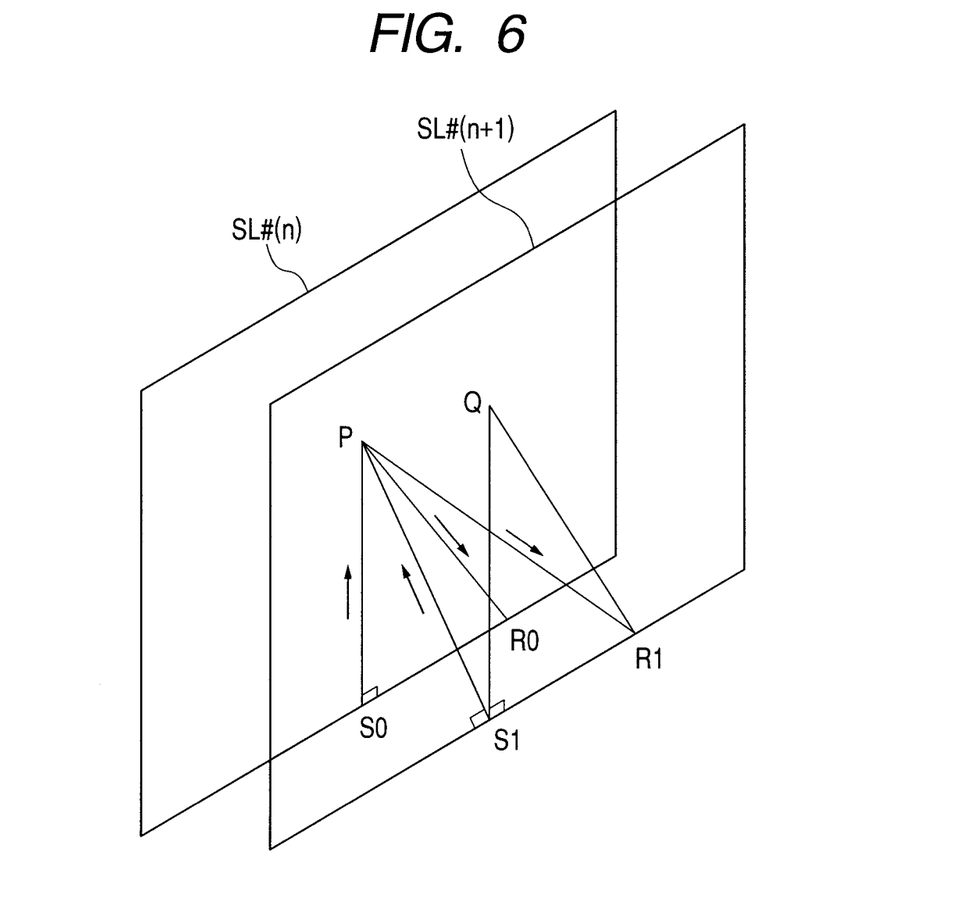
FIG. 6 is an explanatory diagram of a principle of the present invention.

FIG. 6 is a diagram illustrating a principle of the present invention for solving the problem of cost. For a simple description, it is supposed that the target point P is in the plane of the cross-sectional slice SL#(n). The ultrasonic beam emitted at right angles from the center S0 of the transmission and reception element group is reflected at the point P and is received by the transmission and reception elements at a position R0. Next, the probe moves to a position of the cross-sectional slice SL#(n+1), and emits the ultrasonic beam again from the position S1 corresponding to the position S0. The ultrasonic beam is emitted at right angles, and a part thereof also propagates in the direction toward the point P in the cross-sectional slice plane SL#(n), and an ultrasonic wave reflected at the point P is received at the point R1 corresponding to the point R0. The delay and sum of the above-mentioned synthetic aperture method may be realized by adding the reception signal at the point R0 and the reception signal at the point R1 after being adjusted in shift of reception time corresponding to propagation time from transmission via reflection at the point P to reception.

Next, consideration is given to a point Q having a distance from the point S1 in the vertical direction in the cross-sectional slice plane SL#(n+1) that is equal to the distance from the point S1 to the point P. In this case, a triangle having the points S1, P, and R1 at each corner is apparently congruence with a triangle having the points S1, Q, and R1 at each corner. Therefore, the time of propagation from the point S1 via the point P to the point R1 is the same as the time of propagation from the point S1 via the point Q to the point R1. This relationship applies not only to the transmission and reception element at the position of R1 but also to other reception elements in the same transmission and reception element group. Therefore, at the position of the cross-sectional slice plane SL#(n+1), an add signal obtained as a result of the one-dimensional delay and sum with the point P as the focal point may be completely the same to an add signal obtained as a result of the delay and sum with the point Q as the focal point. Therefore, it is understood that the two-dimensional delay and sum with respect to the point P may be realized by performing the one-dimensional delay and sum for each of the cross-sectional slice planes temporarily so as to determine the delay and sum signals of the point P and the point Q, and then performing an appropriate one-dimensional delay and sum in the elevation direction so as to add the delay and sum signals of the point P and the point Q.

The measuring apparatus of Example 1 illustrated in FIG. 2 is an apparatus in which the principle described above is implemented by the real-time process circuit. When the first add signal 10 output from the first delay and sum circuit 9 is supplied to the signal extraction circuit 24, the first add signals concerning the corresponding points in the three slice planes are extracted in parallel. Using the signal output from the signal extraction circuit 24, the second delay and sum circuit 27 performs the delay and sum based on the synthetic aperture method, which is equivalent to performing the two-dimensional delay and sum as described above.

As a result, compared with the case where only the one-dimensional delay and sum is simply performed, the resolution in the elevation direction may be improved. When N number of transmission and reception elements contribute to the two-dimensional delay and sum and there are M number of slice planes, the delay and sum of M×N input signals is necessary in order to directly perform the two-dimensional delay and sum. In contrast, the delay and sum of only M+N input signals is necessary in Example 1. Therefore, compared with the case where the two-dimensional delay and sum is performed directly, the circuit scale may be reduced significantly. Further, because the signal extraction circuit 24 and the second delay and sum circuit 27 operate in parallel as a pipeline, the real-time process may be performed in the same manner as in the case of only the one-dimensional delay and sum.

EXAMPLE 2

Figure 7:
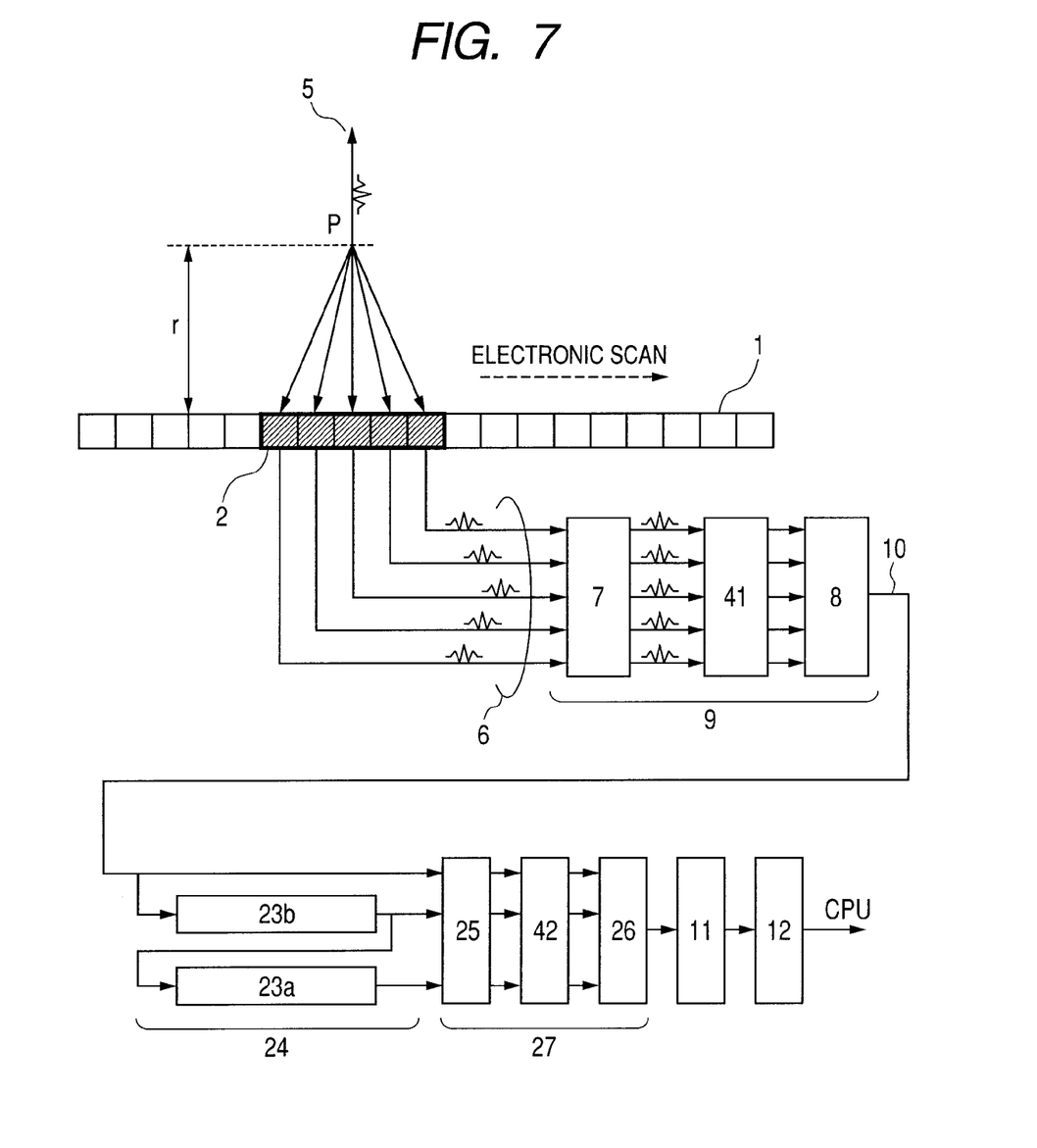
FIG. 7 is a diagram illustrating a structure of a reception process of a measuring apparatus according to Example 2.

FIG. 7 illustrates a structure relating to a reception process performed by a measuring apparatus of Example 2. In Example 2, the delay and sum is performed by the apodizing process in which a weight is added to each signal. The apodizing process is effective for performing optimal adjustment of an aperture size according to a focal point position of the delay and sum, or for reducing influence of an interference acoustic wave entering from other directions. In Example 2, weight multiplying circuits 41 and 42 are additionally provided in the preceding stages of the add circuit 8 of the first delay and sum circuit 9 and the add circuit 26 of the second delay and sum circuit 27, respectively, so that the apodizing process may be performed. The weight in this case may be fixed or may be variable according to signal reception time. Note that in Example 2, the apodizing process is performed in both the first delay and sum circuit 9 and the second delay and sum circuit 27, but the apodizing process may be performed only in either one of the circuits.

EXAMPLE 3

Figure 8:
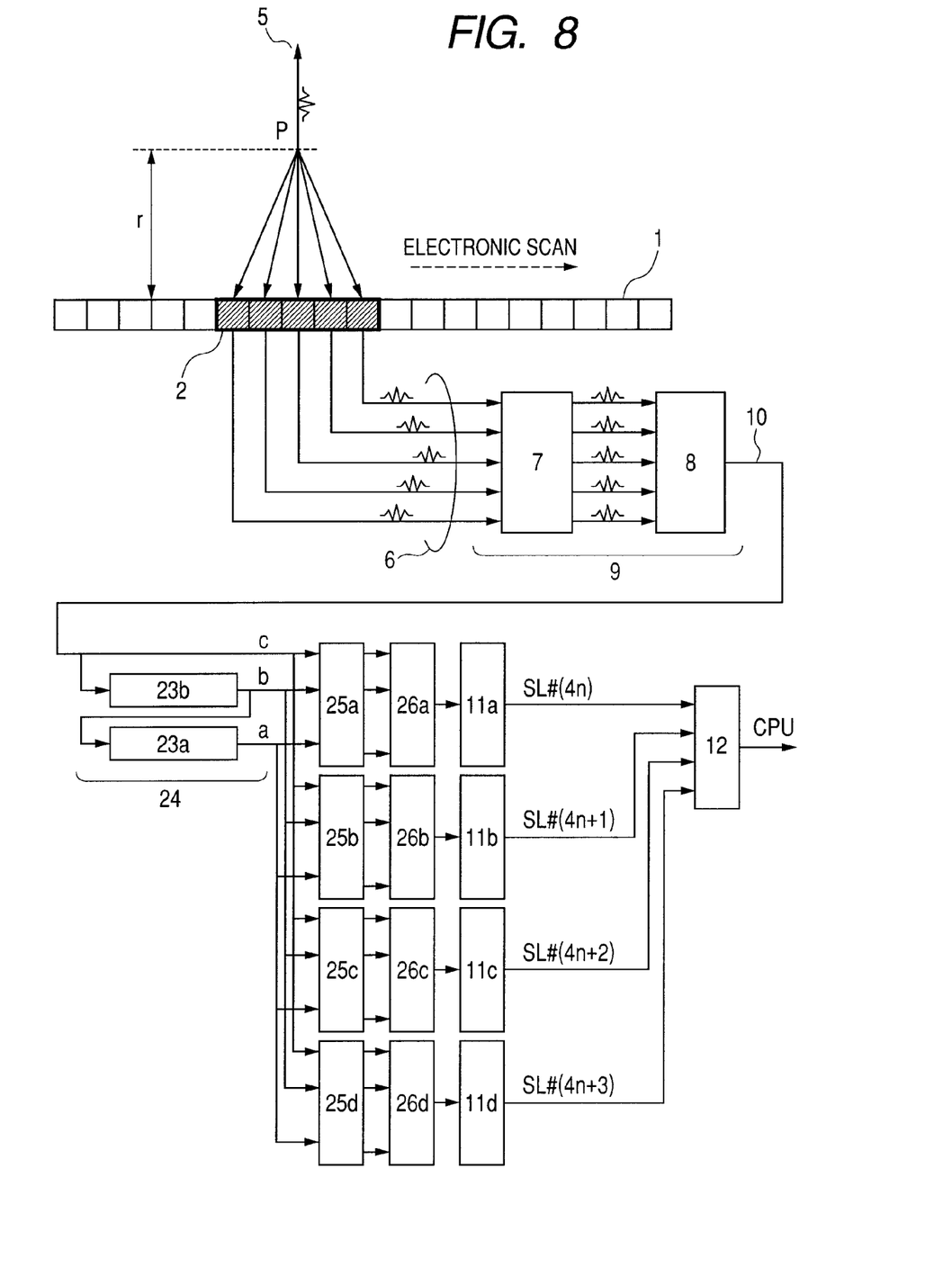
FIG. 8 is a diagram illustrating a structure of a reception process of a measuring apparatus according to Example 3.

FIG. 8 illustrates a structure relating to a reception process performed by a measuring apparatus of Example 3. In Example 3, a plurality of second delay and sum circuits are provided, and the plurality of second delay and sum circuits have different focal point positions serving as a reference of the delay and sum (position in the elevation direction).

Figure 9:
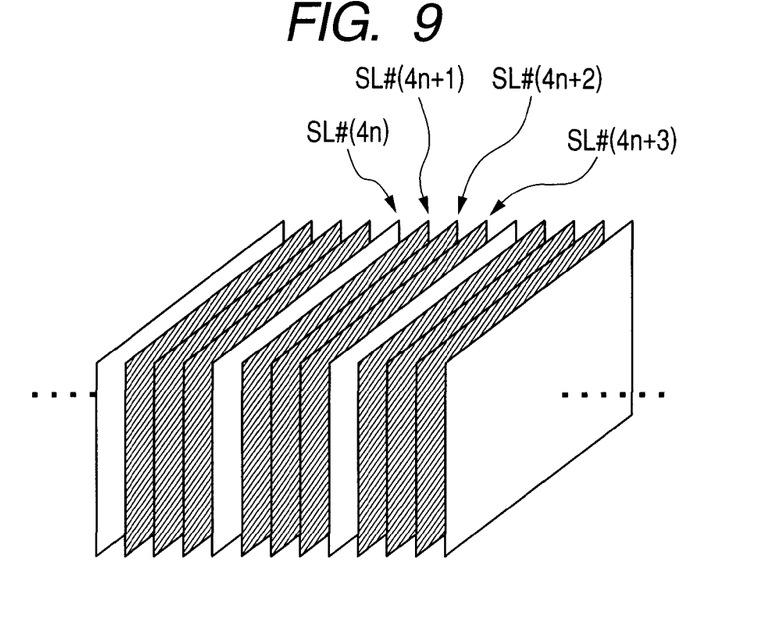
FIG. 9 is a diagram illustrating cross-sectional slice planes that are inserted in Example 3.

In FIG. 6, it is supposed that the focal point P exists in the cross-sectional slice plane obtained by the mechanical scan for a simple description. However, the point P may be at any position in principle. Therefore, in Example 3, the plurality of second delay and sum circuits set the focal point in different cross-sectional slice planes so as to perform the delay and sum process. Specifically, the measuring apparatus of Example 3 includes four second delay and sum circuits constituted of delay adjustment circuits 25a, 25b, 25c, and 25d, and add circuits 26a, 26b, 26c, and 26d. The second delay and sum circuits are each supplied with the same signal from the signal extraction circuit 24. In addition, the outputs of the second delay and sum circuits are supplied to corresponding detection circuits 11a, 11b, 11c, and 11d. With this structure, four cross-sectional slice planes SL#(4n), SL#(4n+1), SL#(4n+2), and SL#(4n+3) are calculated in parallel, and stored in the image memory 12. According to Example 3, as illustrated in FIG. 9, density of the cross-sectional slice planes output from the first delay and sum circuit 9 may be enhanced by four times, so that voxel density of the output three-dimensional echo image data in the elevation direction may be enhanced. Note that the apodizing process may also be performed in Example 3.

EXAMPLE 4

Figure 10:
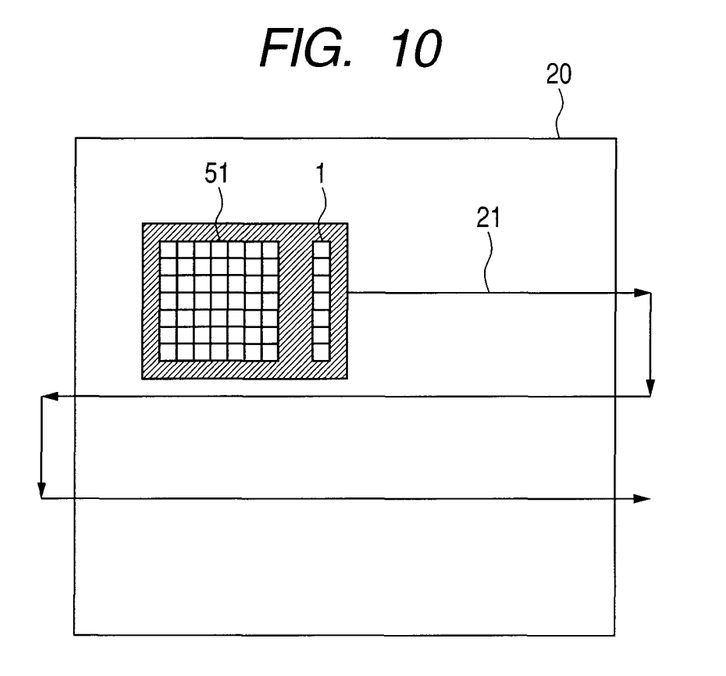
FIG. 10 is a diagram illustrating a probe of a measuring apparatus according to Example 4.

FIG. 10 illustrates Example 4. A measuring apparatus of Example 4 is a photoacoustic mammography apparatus, which mechanically scans an object surface 20 along the route 21 by using a probe in which a two-dimensionally arranged sensor 51 for receiving the photoacoustic wave and the one-dimensional ultrasonic probe 1 are integrated. The photoacoustic mammography apparatus irradiates a pulse-like electromagnetic wave such as a pulse laser to an object and receives a photoacoustic wave induced inside the object by the two-dimensionally arranged sensor 51, so as to generate three-dimensional image data inside the object based on the reception signal. The two-dimensionally arranged sensor of the photoacoustic mammography apparatus receives acoustic waves in parallel in a short time after irradiating the electromagnetic wave. Accordingly, the two-dimensionally arranged sensor is capable of obtaining a high quality signal while moving at a constant speed. Meanwhile, the one-dimensional ultrasonic probe 1 receives echo ultrasonic waves similarly to Examples 1 to 3. Then, similarly to Examples 1, 2, and 3, the two-dimensional delay and sum process is performed on the reception signal, so that high resolution ultrasonic wave image data may be obtained. According to Example 4, the photoacoustic mammography apparatus which may obtain photoacoustic image data in the wide inspection area 20 and the high resolution ultrasonic wave image data at high speed may be formed with ease.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-124888, filed May 25, 2009, which is hereby incorporated by reference herein in its entirety.

The invention claimed is:

1. A measuring apparatus comprising:
   a probe having a plurality of elements each converting acoustic waves into an electric signal, said plurality of elements being arranged at least in a first direction;
   a moving mechanism for moving the probe in a second direction that crosses said first direction;
   a first delay-and-sum circuit for performing delay and summing in said first direction using a plurality of the electric signals obtained by said plurality of elements at individual positions along said second direction, so as to obtain a plurality of first add signals corresponding to a plurality of target points in an object within a slice plane, the slice plane being a plane parallel to said first direction and crossing said second direction;
   a signal extraction circuit wherein the first add signals pass through a plurality of cascaded delay circuits, the signal extraction circuit outputting in parallel a plurality of the first add signals corresponding to one of the target points, wherein the output first add signals are obtained from successive slice planes, and wherein delay times of the cascaded delay circuits are values corresponding to a scanning period for one slice plane;
   a second delay-and-sum circuit for performing delay and summing using the output plurality of first add signals, so as to obtain a second add signal; and
   an image processing circuit for generating image data of inside the object by using a plurality of second add signals corresponding to a plurality of individual target points.

2. A measuring apparatus according to claim 1, wherein said plurality of the electric signals are obtained by electronic scanning.

3. A measuring apparatus according to claim 1, further comprising a plurality of said second delay-and-sum circuits, wherein said plurality of said second delay-and-sum circuits have different target points serving as a reference of the delay and summing.

4. A measuring apparatus according claim 1, wherein at least one or both of said first delay-and-sum circuit and said second delay-and-sum circuit perform the delay and summing with a weight assigned to each signal according to a position where the signal is obtained.

5. A measuring apparatus according to claim 1, wherein the acoustic waves are reflected waves generated when the acoustic waves transmitted from the element are reflected inside the object.

6. A measuring apparatus according claim 1, wherein the acoustic waves are photoacoustic waves induced inside the object irradiated with electromagnetic waves.

7. A measuring apparatus according to claim 1, wherein said moving mechanism continuously moves said probe in said second direction.

8. A measuring apparatus according to claim 4, wherein the weight is fixed.

9. A measuring apparatus according to claim 4, wherein the weight is variable according to a signal reception time.

* * * * *